(12) United States Patent
Zhang

(10) Patent No.: US 7,573,570 B2
(45) Date of Patent: Aug. 11, 2009

(54) COMPACT RAMAN OR FLUORESCENCE EXCITATION SYSTEM

(76) Inventor: Jingyun Zhang, 2490 Partridge Dr., Upper St. Clair, PA (US) 15241

( * ) Notice: Subject to any disclaimer, the term of this patent is extended or adjusted under 35 U.S.C. 154(b) by 39 days.

(21) Appl. No.: 11/894,402

(22) Filed: Aug. 21, 2007

(65) Prior Publication Data

US 2008/0084560 A1 Apr. 10, 2008

Related U.S. Application Data

(60) Provisional application No. 60/839,065, filed on Aug. 21, 2006.

(51) Int. Cl.
*G01J 3/02* (2006.01)
*G01J 3/44* (2006.01)
*G01N 21/64* (2006.01)
*G01N 21/65* (2006.01)

(52) U.S. Cl. .................. 356/301; 356/317; 356/318

(58) Field of Classification Search .................. 356/301
See application file for complete search history.

(56) References Cited

U.S. PATENT DOCUMENTS

| 3,556,659 | A | * | 1/1971 | Hawes ........................ 356/301 |
| 4,076,978 | A | | 2/1978 | Brennan et al. |
| 5,784,507 | A | | 7/1998 | Holm-Kennedy et al. |
| 5,923,423 | A | | 7/1999 | Sawatari et al. |
| 6,069,698 | A | | 5/2000 | Ozawa et al. |
| 2004/0096152 | A1 | | 5/2004 | Nakama et al. |
| 2005/0047724 | A1 | | 3/2005 | Farr |
| 2005/0237642 | A1 | | 10/2005 | Takahashi et al. |

FOREIGN PATENT DOCUMENTS

| EP | 0176625 | 3/1990 |
| JP | 02-039006 | 2/1990 |
| WO | PCT/US2007/018479 | 2/2008 |

* cited by examiner

*Primary Examiner*—F. L Evans
(74) *Attorney, Agent, or Firm*—Morgan Lewis & Bockius LLP

(57) ABSTRACT

A compact Raman and fluorescence spectroscopy system that uses a microprism or micromirror based optical structure to accomplish the introduction of excitation radiation with compactness and simplified system configuration for portable or mobile spectroscopy applications. A microprism may be glued to a surface location of a focusing lens in the system to directly receive the illumination signal without intervening optical components. Alternatively, the microprism may be simply placed in close physical proximity of the focusing lens without being glued thereto. On the other hand, a micromirror may be used instead of the microprism. The illuminating photons received by the microprism or micromirror may be directly transferred to the sample under investigation via the focusing lens. The compact system may be made portable and may further include an on-board spectrometer with or without a display unit. For chemical detecting applications, a detector (e.g., a CCD array) may also be provided along with the spectrometer.

15 Claims, 5 Drawing Sheets

COMPACT RAMAN OR FLUORESCENCE EXCITATION SYSTEM

REFERENCE TO RELATED APPLICATION

The disclosure in the present application claims priority benefit under 35 U.S.C. § 119(e) of the U.S. Provisional Application No. 60/839,065, titled "Compact Spectroscopy System," and filed on Aug. 21, 2006, the disclosure of which is incorporated herein by reference in its entirety.

BACKGROUND

Field of the Disclosure

The present disclosure generally relates to spectroscopy systems and, more particularly, to a compact, hand-held spectroscopic unit for in-field Raman, fluorescence, or other chemical detection applications.

BRIEF DESCRIPTION OF RELATED ART

Some modern spectroscopy applications require handheld or portable spectroscopy systems that can be employed in the field and can be easily transported from one testing location to another. For example, a law enforcement department may need a mobile spectroscopy unit that can be easily carried to a threat location (e.g., a location where an anthrax threat may be present) for on-the-spot decision making using spectral analysis techniques. In handheld or mobile spectroscopy (e.g., Raman spectroscopy, fluorescence spectroscopy, etc.), it is therefore desirable to have a lightweight and compact spectroscopy system that is not only easily portable, but also without any loss of performance attributable to its mobile nature or compactness.

FIG. 1 illustrates an exemplary prior art Raman spectroscopy system 10 for portable or handheld applications. The system 10 of FIG. 1 is traditionally employed in the field to detect, for example, hazardous biothreat (e.g., anthrax) or chemical agents (e.g., ricine or other poison) using principles of Raman spectroscopy. In the system of FIG. 1, a laser diode 12 may be used to provide an oblique illumination onto a mirror 14. The laser illumination reflected from the mirror 14 is then focused onto a sample 20 under investigation using a combination of a longpass filter 16 and a focusing lens (Lens-1) 18. The longpass filter 16 serves to reflect the incident laser light towards Lens-1 during sample illumination, and to pass all Raman scattered light received from the sample 20 to a collecting lens 24 (Lens-2) during the Raman signal collection phase. An additional lens (not shown in FIG. 1) may be placed between the laser diode 12 and the mirror 14 to manipulate the shape or size of the laser illumination on the sample 20.

In the system 10 of FIG. 1, the Raman scattered light from the sample is initially collected by focusing lens 18, "cleaned" by the 6.5° longpass filter 16 (which blocks some photons having the illuminating laser wavelength) and a 0° filter 22 (which further blocks photons having the illuminating laser wavelength), and then focused onto an entrance slit 26 of a spectrometer 28 by the collecting lens (Lens-2) 24. In FIG. 1, the laser illumination path is indicated by a solid line whereas the propagation of Raman scattered light is indicated by the dotted lines. The spectrometer 28 may be a gratings-based dispersive spectrometer, which may measure the Raman spectrum of the sample 20 using the photons received at its entrance slit 26 and provide further spectral analysis of the sample 20 as selected by a user of the portable spectroscopy system 10. Various components in the system 10 in FIG. 1 and their functionalities are known to one skilled in the art, and, hence, a detailed description of the system 10 is not provided herein.

It is observed with reference to the Raman spectroscopy system 10 in FIG. 1 that certain spatial relationship among various components in the system has to be maintained for the system to operate effectively. For example, a minimum separation of 26 mm may be required between the focusing lens 18 and the first filter (i.e., the 6.5° longpass filter 16) so as to maintain a predetermined 13° angle of incidence of illumination light beam BC and its proper reflection by the longpass filter 16 along the lens axis AB. Because of the 6.5° tilt (from the vertical) of the longpass filter 16, an improper separation between the focusing lens 18 and the longpass filter 16 may result in misalignment or improper focusing of the incident illumination from the laser diode 12. Also, the more the number of system components in the system 10, the harder it becomes to establish a compact geometry for the system 10 because of the constraints placed by components' physical dimensions and the minimum separation required between various components for accurate optical measurements.

It is therefore desirable to devise a portable spectroscopy system (for Raman and fluorescence spectroscopy applications) that uses significantly less components than traditional portable spectroscopy systems (e.g., the system 10 in FIG. 1) and that is substantially less constrained by minimum physical separation requirements for its constituent components. It is also desirable that such a compact, mobile spectroscopy unit provide performance that is at least comparable to that of a traditional portable spectroscopy system.

SUMMARY

In one embodiment, the present disclosure relates to a system that comprises an illumination source for providing a plurality of illuminating photons in a first direction of propagation; and a microprism optically coupled to the illumination source to directly receive therefrom the plurality of illuminating photons in the first direction and to direct the received illuminating photons in a second direction of propagation. The system also comprises a focusing lens physically proximate to the microprism and optically coupled thereto, wherein the focusing lens is configured to directly receive the plurality of illuminating photons from the microprism in the second direction and to focus the illuminating photons onto a focusing location.

In an alternative embodiment, the present disclosure contemplates a system that uses a micromirror instead of a microprism in a manner similar to that discussed in the preceding paragraph.

In a further embodiment, the present disclosure relates to a method that comprises configuring an illumination source to provide a plurality of illuminating photons in a first direction of propagation; and changing direction of propagation of the plurality of illuminating photons from the first direction to a second direction of propagation using only a microprism or a micromirror. The method also comprises receiving the illuminating photons directly from the microprism or the micromirror in the second direction of propagation and focusing the illuminating photons onto a focusing location.

In one embodiment, the present disclosure relates to a compact Raman and fluorescence spectroscopy system that uses a microprism or micromirror based optical structure to accomplish the introduction of excitation radiation with compactness and simplified system configuration for portable or mobile spectroscopy applications. A microprism may be glued to a surface location of a focusing lens in the system to directly receive the illumination signal without intervening optical components. In one embodiment, the microprism may be simply placed in close physical proximity to the focusing lens without being glued thereto. On the other hand, a micromirror may be used instead of a microprism. The illuminating photons received by the microprism or micromirror may be directly transferred to the sample under investigation via the focusing lens. The compact system may be made portable and may further include an on-board spectrometer with or without a display unit. For chemical detecting applications, a detector (e.g., a CCD detector) may also be provided along with the spectrometer.

BRIEF DESCRIPTION OF THE DRAWINGS

For the present disclosure to be easily understood and readily practiced, the present disclosure will now be described for purposes of illustration and not limitation, in connection with the following figures, wherein.

DETAILED DESCRIPTION

The accompanying figures and the description that follows set forth the present disclosure in embodiments of the present disclosure. However, it is contemplated that persons generally familiar with optics, operation and maintenance of optical instruments (including spectroscopic instruments), or optical spectroscopy will be able to apply the teachings of the present disclosure in other contexts by modification of certain details. Accordingly, the figures and description are not to be taken as restrictive of the scope of the present disclosure, but are to be understood as broad and general teachings. In the discussion herein, when any numerical range of values is referred or suggested, such range is understood to include each and every member and/or fraction between the stated range of minimum and maximum.

Figure 1:
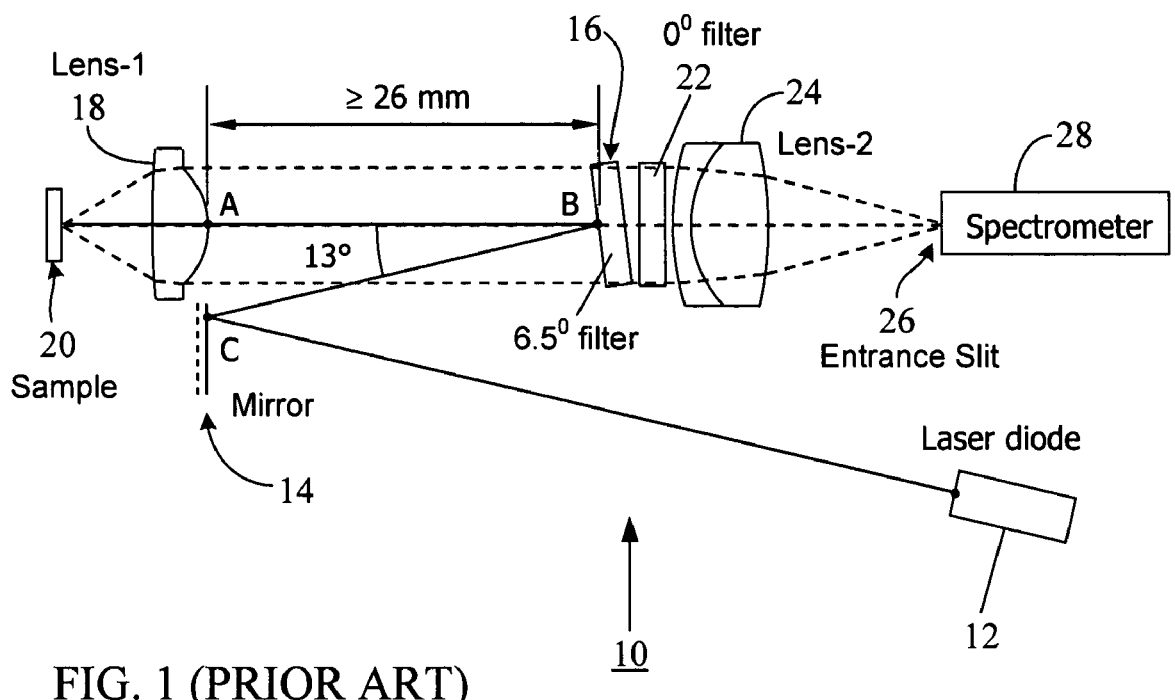
FIG. 1 illustrates an exemplary prior art Raman spectroscopy system for portable or handheld applications.
Figure 2:
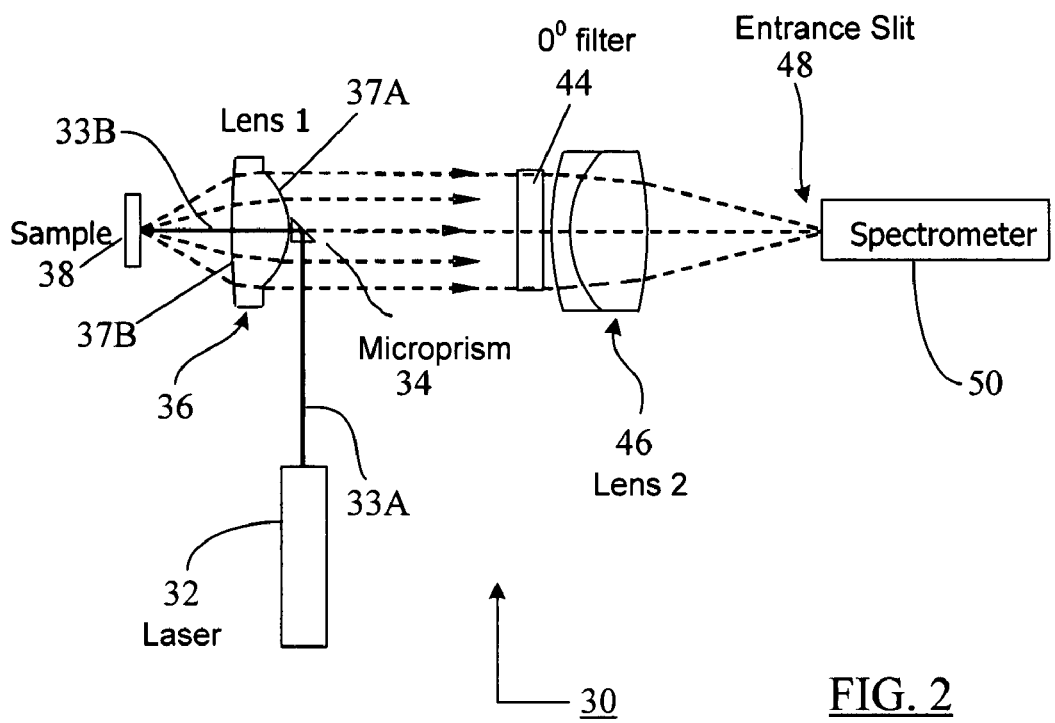
FIG. 2 depicts an exemplary microprism-based compact and portable Raman or fluorescence spectroscopy system according to one embodiment of the present disclosure.

FIG. 2 depicts an exemplary microprism-based compact and portable Raman or fluorescence spectroscopy system 30 according to one embodiment of the present disclosure. In the embodiment of FIG. 2, the mirror 14 and the longpass filter 16 of FIG. 1 are replaced by a microprism 34 suitably placed to directly receive the illuminating photons from an illumination or excitation source 32. Thus, in the system 30 of FIG. 2, there is no intervening optical element or structure between the illumination source 32 and the microprism 34, thereby allowing a more compact geometry for the system 30. The system 30 may be used in various spectroscopy applications including, for example, Raman spectroscopy and fluorescence spectroscopy. A suitable excitation source 32 may be selected for the desired spectroscopy application as is known to one skilled in the art. In one embodiment, the illumination source 32 is a 532 nm laser diode. In alternative embodiments, the illumination source 32 may provide illuminating photons with wavelengths other than 532 nm and may include wavelengths in the ultraviolet (UV) region, visible light region, or the infrared (including NIR and far infrared) region of the electromagnetic spectrum. Depending on the desired spectroscopy application, another suitable illumination or excitation source may include, for example, a UV LED (light emitting diode).

It is noted here that in the discussion herein the terms "illumination," "illuminating," and "excitation" are used interchangeably as can be evident from the context. For example, the terms "illumination source" and "excitation source" are used interchangeably. Similarly, the terms "illuminating photons" and "excitation photons" are also used interchangeably. Furthermore, the terms "Raman or fluorescence" and "Raman and fluorescence" are used interchangeably to indicate that various systems described herein may be used for Raman and/or fluorescence spectroscopy applications as desired.

In the embodiment of FIG. 2, the illuminating or excitation photons (from the illumination source 32) travel along an illumination path depicted by straight lines, whereas a photon collection path is indicated by dotted lines and arrows. The photon collection path may carry photons emitted, reflected, or scattered by a sample 38 upon receiving illumination photons from the illumination source 32. The sample 38 may be placed at a focusing location where illuminating photons are focused by a focusing lens 36. In one embodiment, a point or a narrow area on the surface of the sample 38 (e.g., a sample region of interest (ROI)) may be illuminated by the focused light beam (from the focusing lens 36). In another embodiment, the lens 36 may be configured to provide a wide-field illumination on the surface of the sample 38. It is noted here that the depiction of various propagation paths using solid and dotted lines in FIG. 2 (and also in FIGS. 3-8, as applicable) is for illustrative purpose only. The depiction should not be construed to illustrate any actual optical signal propagation paths. In practice, the illumination and collection signal paths may be different from those shown in FIG. 2 and may not be as clearly defined as in the illustration in FIG. 2.

In the system 30 of FIG. 2, the microprism 34 is a 90° (right-angle) microprism. The right-angle microprism 34 may be epoxy-glued to a lens surface 37A that is physically closest to the microprism 34 as shown in FIG. 2. In one embodiment, a right-angle forming side of the microprism 34 may be glued to a central location (or to a substantially flat portion of the central location) on the lens surface 37A. Additional details of the right-angle microprism 34 are provided hereinbelow in conjunction with discussion of FIG. 3. It is noted that the other lens surface 37B remains closer to the sample 38 placed at the focusing location (or focal point) of the lens 36. A convex structure is shown for the focusing lens 36 in FIG. 2. However, any other suitable lens design may be selected as per the desired application by one skilled in the art.

The illuminating photons from the laser 32 may travel along a first direction of propagation indicated by reference numeral "33A" in FIG. 2. The right-angle microprism 34 may directly receive the illuminating photons along this first direction 33A and direct them to the focusing lens 36 along a second direction of propagation indicated by reference numeral "33B." Because there is no intervening optical element between the microprism 34 and the focusing lens 36, the focusing lens 36 directly receives the illuminating photons sent by the microprism 34 in the second direction of propagation 33B. The focusing lens 36 then focuses the received illumination onto a focusing location (not shown), where the sample 38 may be placed to provide the necessary sample illumination for the spectroscopy application at hand.

It is observed with respect to the system 30 in FIG. 2 that the first direction of propagation 33A and the second direction of propagation 33B are at substantially right-angle to each other. However, in alternative embodiments, different angles other than 90° may be present between the propagation paths of photons received by the microprism 34 from the laser source 32 and those received by the focusing lens 36 from the microprism 34. In the embodiment of FIG. 2, the laser 32 is shown to provide illuminating photons to the right-angle microprism 34 in a substantially vertical direction. However, non-vertical or oblique illumination may be provided as discussed later in conjunction with, for example, FIGS. 5-6.

The spectral data-containing signals from the sample 38 (e.g., Raman scattered light, or fluorescence light) may be initially collected by the focusing lens 36 and transferred to a collection lens 46 (Lens-2) via a 0° filter 44 as shown in FIG. 2. In one embodiment, the collection lens 46 and the 0° filter 44 may comprise an optical signal "collection optics." As noted before in the "Background" section, the 0° filter 44 may function as a laser line rejection filter so as to prevent photons having the laser illumination wavelength from reaching the collecting lens 46. Hence, only those photons (scattered or emitted) that are resulting from interaction of the illuminating photons with the sample material are allowed to pass through the filter 44 so as to obtain true spectral characteristic of the sample 38 without interfering effects from the original illuminating photons. The photons reflected from the sample 38 may have the wavelength of the excitation photons and, hence, may be blocked by the rejection filter 44 even if initially collected by the focusing lens 36 and transferred to the filter 44.

The collection lens 46 may provide the received photons to a spectral analysis system to obtain, for example, a spectrum of the sample under investigation to analyze the sample content in more detail. In one embodiment, the spectral analysis system may include a gratings-based dispersive spectrometer 50 with an entrance slit 48. The spectral data-containing signals received at the slit 48 (from the collection lens 46) of the spectrometer 50 are dispersed by the spectrometer gratings (not shown) to provide wavelength-specific spectral content of the photons received from the illuminated sample 38. A spectral imaging system in conjunction with a liquid crystal-based tunable filter and a CCD detector is discussed hereinbelow with reference to the discussion of the exemplary embodiment in FIG. 7.

It is evident from a comparison of the system configurations in FIGS. 1 and 2 that the microprism-based portable spectroscopy system 30 in FIG. 2 is structurally significantly less complex and more compact than the system 10 in FIG. 1. Because of the absence of the physically larger and space-consuming laser illumination-directing assembly (i.e., the 6.5° filter 16 and the mirror 14 in FIG. 1) in the system of FIG. 2, the physical separation between the focusing lens 36 and the collection lens 46 can be significantly reduced (e.g., by as much as 80% or more) from the minimum 26 mm requirement in case of the system 10 in FIG. 1, thereby resulting in a more compact assembly in case of the system 30 in FIG. 2. Furthermore, the physical closeness of Lens-1 (36) and Lens-2 (46) in the embodiment of FIG. 2 results in less spreading or loss of light (reflected, scattered, or emitted) received from the sample 38 and being sent to the spectrometer 50. This may, in turn, result in reduction in incident laser power and/or spectrometer power requirements in the system 30 of FIG. 2 to accomplish at least a comparable spectroscopic performance as that of the system 10 in FIG. 1.

Figure 3:
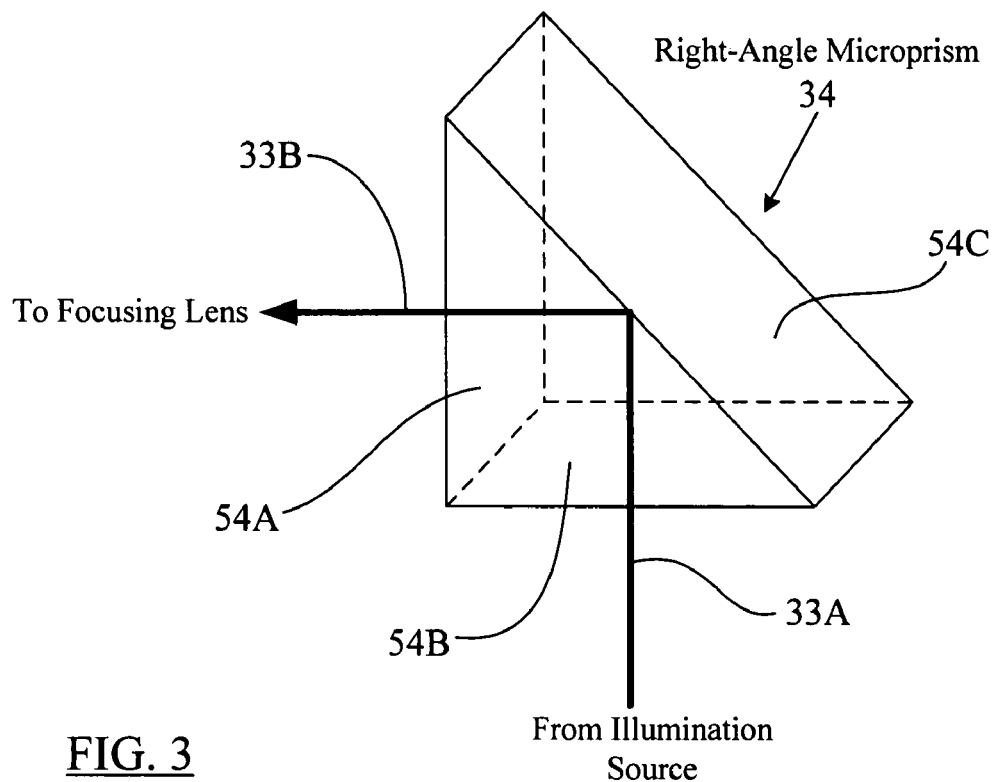
FIG. 3 illustrates exemplary details of excitation radiation propagation through the right-angle microprism in the system of FIG. 2.

FIG. 3 illustrates exemplary details of excitation radiation propagation through the right-angle microprism 34 in the system 30 of FIG. 2. The right-angle microprism 34 is shown to have three non-triangular sides and two triangular sides. The three non-triangular sides include two right-angle forming sides 54A and 54B, and a side 54C that is opposite to the right angle. Each of the two triangular sides connects to a respective edge of each of the three non-triangular sides to form the three-dimensional prism structure as shown in FIG. 3. In the embodiment of FIG. 2, one of the right-angle forming sides (e.g., the side 54A) is shown glued to a substantially flat portion at a central location on the lens surface 37A. In that configuration (which is illustrated in more detail in FIG. 3), a light beam 33A from the illumination source 32 may first enter the microprism 34 through the bottom side 54B. The incoming light beam 33A may then get reflected by the non-right-angle-forming side 54C and the reflected beam 33B may come out of the side 54A (which is glued to the lens 36) to be focused by the focusing lens 36 as illustrated in FIG. 3. It is noted here that the details of the microprism structure and the propagation of excitation photons in FIG. 3 are for illustrative purpose only. In actual operation, different microprism geometries and excitation signal propagation configurations may be present.

Figure 4:
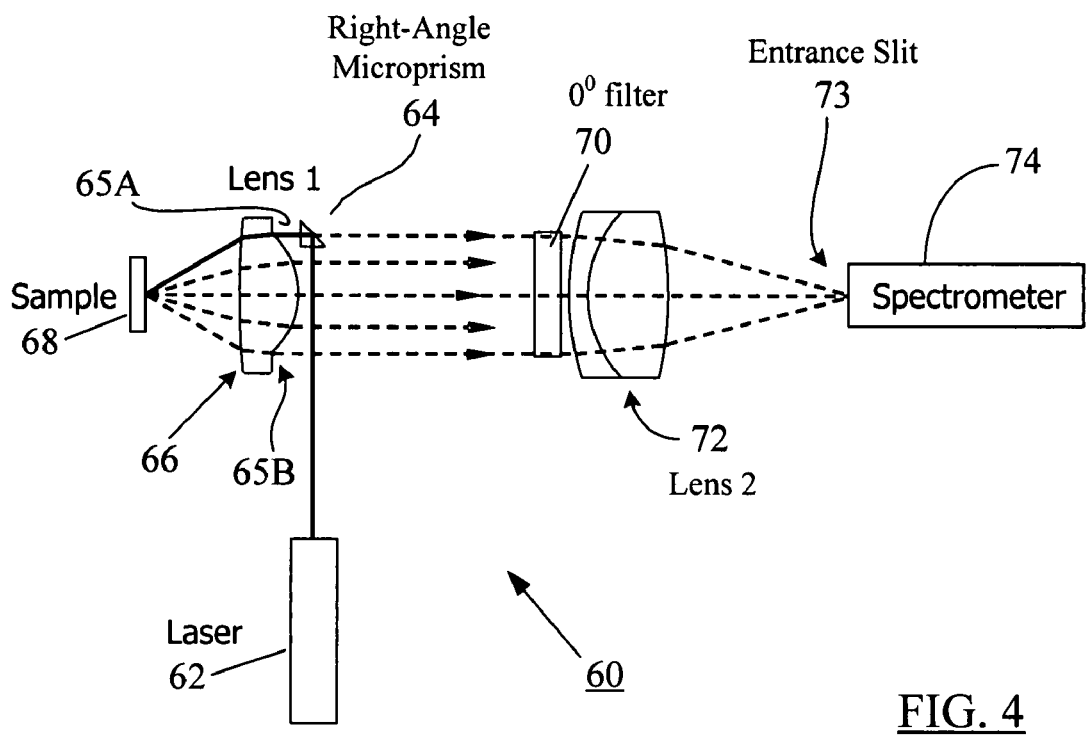
FIG. 4 shows an exemplary microprism-based compact Raman or fluorescence spectroscopy system according to another embodiment of the present disclosure.

FIG. 4 shows an exemplary microprism-based compact Raman or fluorescence spectroscopy system 60 according to another embodiment of the present disclosure. As in the system 30 of FIG. 2, the system 60 in FIG. 4 also includes an illumination source 62, right-angle microprism 64, a focusing lens 64, a sample 68 (which can be placed at a focusing location when needed to be analyzed), a laser line rejection filter 70, a collection lens 72, and a dispersive spectrometer 74 with an optical signal entrance slit 73. Similar to FIG. 2, FIG. 4 also depicts the propagation path of illuminating photons by a solid line and the propagation path of optical signals received from the sample (when illuminated) by dotted lines and arrows. Furthermore, in an alternative embodiment, a detector (not shown) in conjunction with an optical tunable filter (e.g., an LCTF) may be used instead of (or in addition to) the dispersive spectrometer 74 in the system 60 in FIG. 4. An exemplary LCTF-based embodiment is discussed later hereinbelow with reference to FIG. 7. The discussion of functionality of all of the components shown in FIG. 4 is already provided hereinbefore with reference to the discussion of the embodiment in FIG. 2 and, hence, is not repeated here for the sake of brevity.

Contrary to the configuration in FIG. 2, the right-angle microprism 64 in the system 60 of FIG. 4 is not placed near or glued to a central portion of a lens surface of the focusing lens 66. Instead, the microprism 64 may be placed near a top edge 65A of the focusing lens 66 that is physically closest to the microprism 64. In another embodiment, the right-angle microprism 64 could be similarly placed (not shown) near the bottom edge 65B instead of the top edge 65A. The microprism 64 in FIG. 4 may be placed within the numerical aperture (NA) of the focusing lens 66 so as to be able to direct the laser illumination onto the focusing location where the sample is placed. In the embodiment of FIG. 4, because of the lens curvature, the microprism 64 may not be glued at the edge 65A of the lens 66, but, instead, may be held in its place close to the edge 65A using a mechanical holding structure (not shown). In an alternative embodiment, a right-angle forming surface (not shown) of the right-angle microprism 64 may be glued (e.g., using epoxy and in a manner similar to that shown in the embodiment of FIG. 2) to a substantially flat surface at the top (or bottom) edge of the lens 66 to deliver the laser excitation to the lens 66 and onto the sample 68.

As in the embodiment of FIG. 2, in FIG. 4, the laser illumination is first directly applied to the microprism 64 in the vertical direction. The illumination is then deflected onto the sample region of interest (ROI) via the combined optical effects of the microprism 64 and the focusing lens 66 as illustrated in FIG. 4. However, a non-vertical (oblique) laser illumination (not shown) may be achieved, for example, by appropriately placing the right-angle microprism 64 at or near an edge (e.g., the top edge 65A) of the focusing lens 66. Some other types of optical structures and corresponding oblique illumination-based embodiments are discussed later hereinbelow with reference to FIGS. 5-6.

It is observed here that a 90° (right-angle) microprism made of optical glass and manufactured by Edmund Optics of NJ, USA, may be used in the embodiments of FIGS. 2 and 4.

Figure 5:
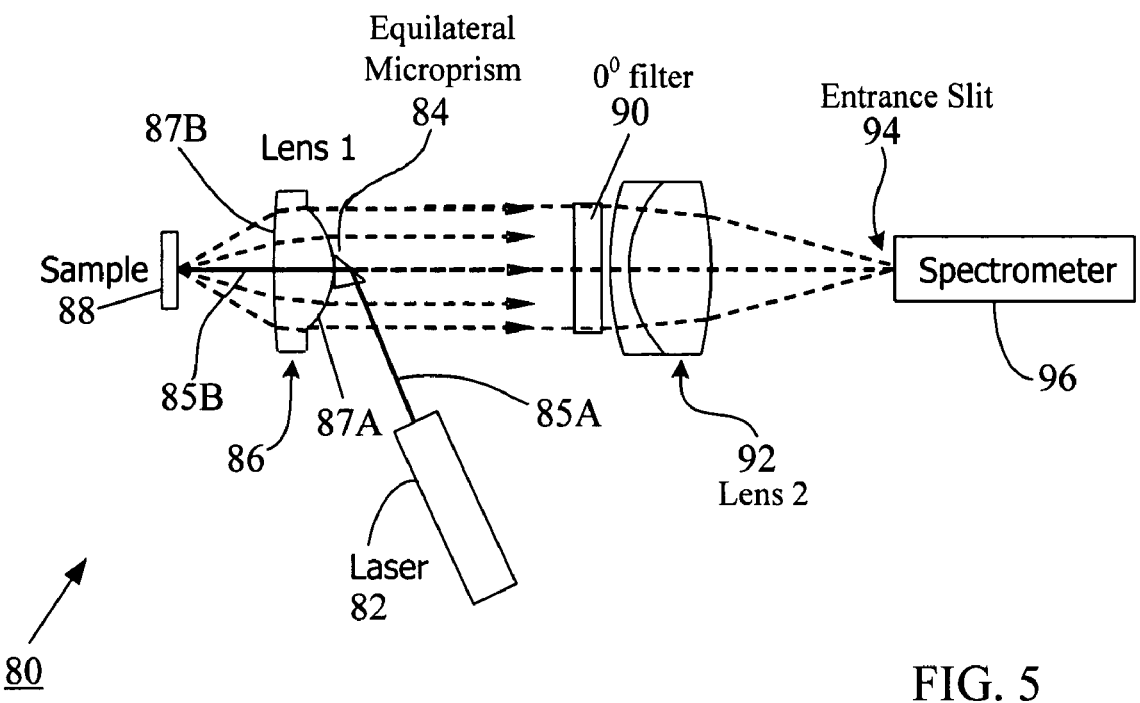
FIG. 5 depicts an equilateral microprism-based compact and portable Raman or fluorescence spectroscopy system according to an exemplary embodiment of the present disclosure.

FIG. 5 depicts an equilateral microprism-based compact and portable Raman or fluorescence spectroscopy system 80 according to an exemplary embodiment of the present disclosure. Thus, instead of a right-angle microprism in the embodiments of FIGS. 2 and 4, the system 80 of FIG. 5 uses an equilateral microprism 84 (with three equal sides) to directly receive the laser illumination (which may be an oblique illumination) as discussed later below. However, as in the system 30 of FIG. 2, the system 80 in FIG. 5 also includes an illumination source 82, a focusing lens 86, a sample 88 (which can be placed at a focusing location when needed to be analyzed), a laser line rejection filter 90, a collection lens 92, and a dispersive spectrometer 96 with an optical signal entrance slit 94. Instead of a dispersive spectrometer 96, a tunable filter and CCD detector (not shown here, but shown in FIG. 7) may be used in the system 80 as similarly observed with reference to discussion of FIGS. 2 and 4. Furthermore, similar to FIG. 2, FIG. 5 also depicts the propagation path of illuminating photons by a solid line and the propagation path of optical signals received from the sample (when illuminated) by dotted lines and arrows. The discussion of functionality of all of the components shown in FIG. 5, except the equilateral microprism 84, is already provided hereinbefore with reference to the discussion of the embodiments in FIGS. 2 and 4 and, hence, is not repeated here for the sake of brevity.

In the embodiment of FIG. 5, the equilateral microprism 84 is shown attached (e.g., epoxy-glued) to a central location of a lens surface 87A of the focusing lens 86 that is physically closest to the microprism 84. One side of the microprism 84 (e.g., the side 98A shown in FIG. 6 discussed later hereinbelow) may be glued to a substantially flat portion on the central location of the lens surface 87A. The other lens surface 87B remains closer to the focusing location where the sample 88 may be placed. In the embodiment of FIG. 5, the use of the equilateral microprism 84 may allow for an oblique laser illumination as opposed to the vertical laser illuminations in the embodiments of FIGS. 2 and 4. As shown in FIG. 5, the illuminating photons from the illumination source 82 (e.g., a laser diode) may travel along the illumination path 85A, which is at an oblique angle to a light receiving surface (e.g., the surface 98C in FIG. 6) of the equilateral microprism 84. The incoming photons may be then deflected by the microprism 84 along a second direction of propagation 85B for focusing on the sample 88 using the lens 86.

Figure 6:
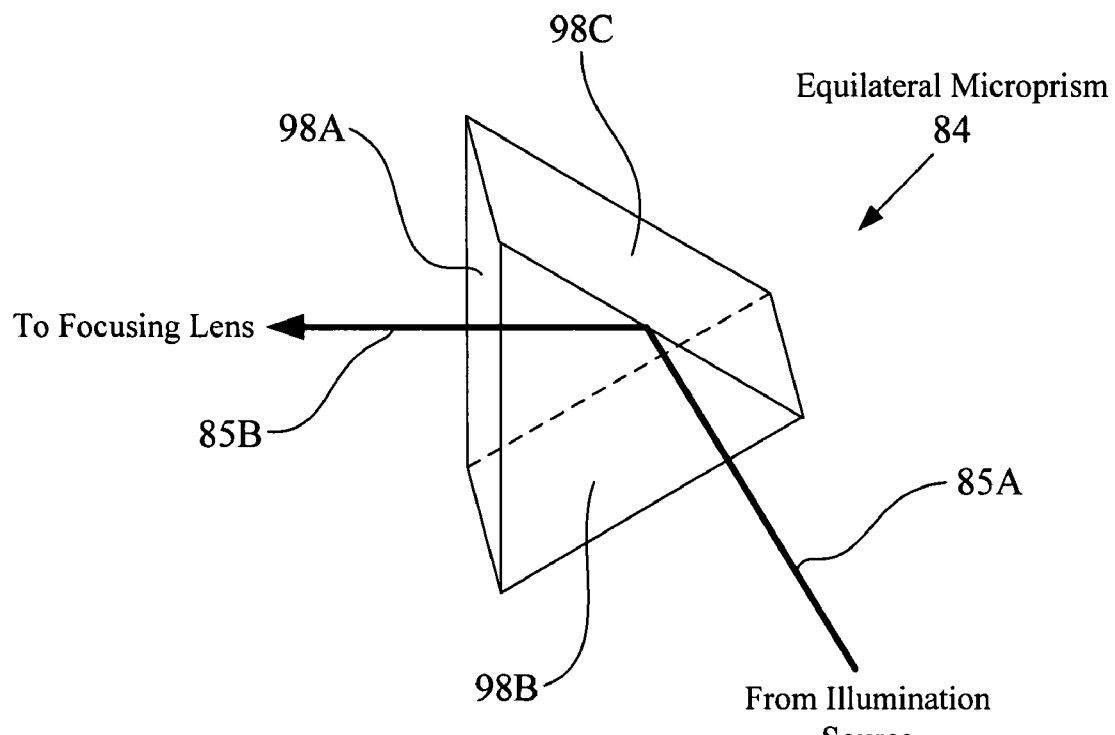
FIG. 6 illustrates exemplary details of excitation radiation propagation through the equilateral microprism in the system of FIG. 5.

FIG. 6 illustrates exemplary details of excitation radiation propagation through the equilateral microprism 84 in the system 80 of FIG. 5. The equilateral microprism 84 is shown to have three non-triangular sides and two triangular sides. The three non-triangular sides are identified in FIG. 6 by reference numerals 98A, 98B, and 98C. Each of the two triangular sides connects to a respective edge of each of the three non-triangular sides to form the three-dimensional prism structure as shown in FIG. 6. In the embodiment of FIG. 5, one of the non-triangular sides (e.g., the side 98A) is shown glued to a substantially flat portion at a central location on the lens surface 87A. In that configuration (which is illustrated in more detail in FIG. 6), an oblique light beam 85A from the illumination source 82 may first enter the microprism 84 through the bottom side 98B. The incoming light beam 85A may then get reflected by the non-triangular side 98C and the reflected beam 85B may come out of the side 98A (which is glued to the lens 86) to be focused by the focusing lens 86 as illustrated in FIG. 6. It is noted here that the details of the microprism structure and signal propagation in FIG. 6 are for illustrative purpose only. In actual operation, different microprism geometries and signal propagation configurations may be present. In one embodiment, for example, an equilateral microprism-based system configuration (not shown) similar to that illustrated in FIG. 4 with respect to a right-angle microprism may also be obtained. In that configuration, the equilateral microprism 84 may not be glued to the lens surface 87A, but, rather, may be placed in a close physical proximity of the lens surface 87A (in a way similar to that illustrated in FIG. 4 for the microlens 64) to achieve desired signal propagation and focusing. Oblique illumination may still be possible even when the equilateral microprism 84 is physically separate from the lens 86.

It is noted that, in one embodiment, an equilateral microprism made of optical glass and manufactured by Edmund Optics of NJ, USA, may be used in the embodiment of FIG. 6.

Figure 7:
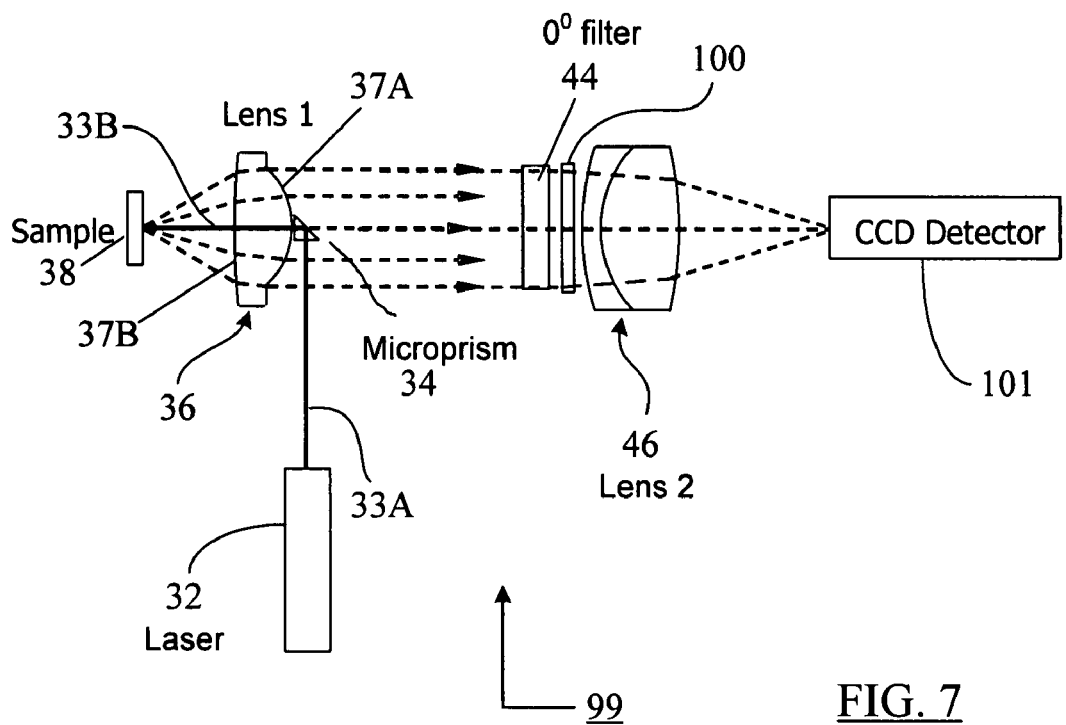
FIG. 7 depicts an exemplary microprism-based compact and portable Raman or fluorescence spectroscopy system according to one embodiment of the present disclosure using a liquid crystal-based tunable filter.

FIG. 7 depicts an exemplary microprism-based compact and portable Raman or fluorescence spectroscopy system 99 according to one embodiment of the present disclosure using a liquid crystal-based tunable filter (e.g., an LCTF) 100. For the sake of simplicity and ease of illustration only, the embodiment in FIG. 7 is shown to be substantially similar to that in FIG. 2 and, in the embodiment of FIG. 7, various system elements common between the embodiments in FIGS. 2 and 7 are depicted using the same reference numerals as are used for the identical elements in the embodiment of FIG. 2. Therefore, additional discussion of these common system elements is not provided herein. In the embodiment of FIG. 7, the LCTF 100 is shown placed between the 0° filter 44 and the collection lens 46. The LCTF 100 may be tuned to a desired wavelength or over a range of desired wavelengths. The filtered photons output from the LCTF may include only those photons (from all the photons received from the 0° filter 44) that have a wavelength to which the liquid crystal tunable filter 100 is tuned. A CCD (charge coupled device) detector 101 may be used to receive the filtered photons from the LCTF 100 to obtain a wavelength-specific spectral information for the sample 38 under investigation. The detector 101 may generate signal data that can be used to display a wavelength-specific spectral image of the sample 38.

In one embodiment, a multi-conjugate filter (MCF) may be used instead of a simple LCTF (e.g., the LCTF 100) to provide more precise wavelength tuning of photons received from the sample 38. Some exemplary multi-conjugate filters are discussed, for example, in U.S. Pat. No. 6,992,809, titled "Multi-Conjugate Liquid Crystal Tunable Filter;" and in the United States Published Patent Application Number US2007/0070260A1, titled "Liquid Crystal Filter with Tunable Rejection Band," the disclosures of both of these publications are incorporated herein by reference in their entireties.

Figure 8:
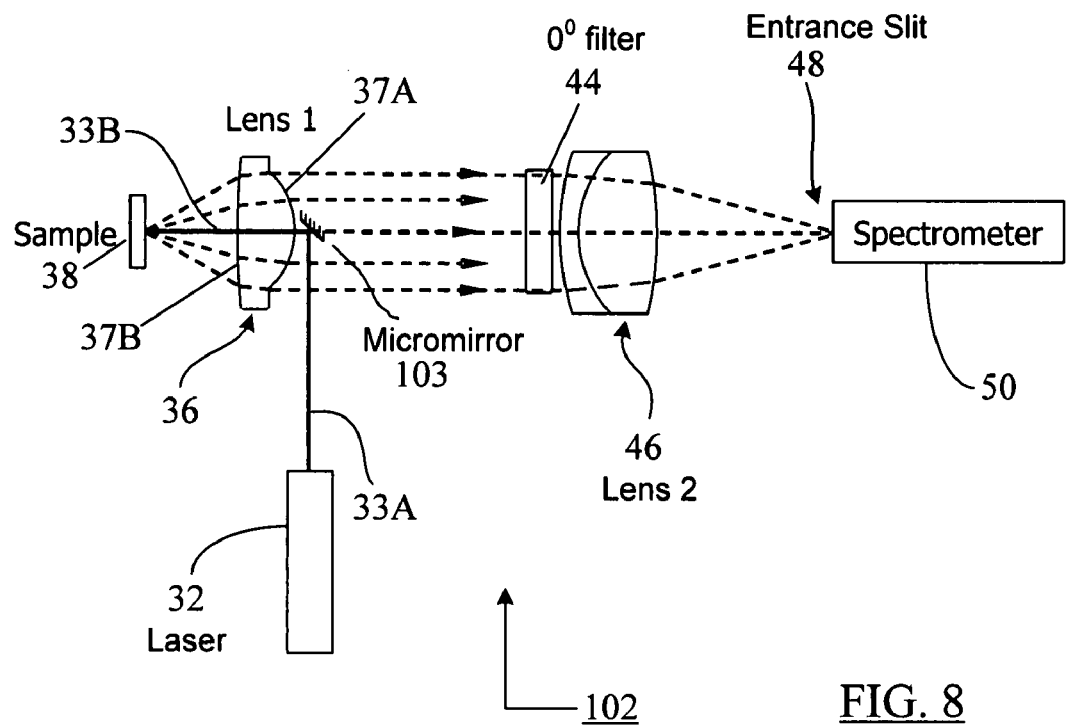
FIG. 8 shows an exemplary micromirror-based compact Raman or fluorescence spectroscopy system according to one embodiment of the present disclosure.

In one embodiment, a micromirror may be used instead of a microprism. FIG. 8 shows an exemplary micromirror-based compact Raman or fluorescence spectroscopy system 102 according to one embodiment of the present disclosure. For the sake of simplicity and ease of illustration only, the embodiment in FIG. 8 is shown to be substantially similar to that in FIG. 2 and, in the embodiment of FIG. 8, various system elements common between the embodiments in FIGS. 2 and 8 are depicted using the same reference numerals as are used for the identical elements in the embodiment of FIG. 2. Therefore, additional discussion of these common system elements is not provided herein. In the embodiment of FIG. 8, a micromirror 103 is shown placed in physical proximity of a central portion of the lens surface 37A instead of the microprism 34 (in the embodiment of FIG. 2). Similar to the embodiment in FIG. 4, the micromirror 103 may be alternatively placed near a top or bottom edge of the lens surface 37A. Additional or alternative configurations may be similarly devised. As before, the other lens surface 37B may remain physically close to the focusing location where a sample may be placed for analysis. Similar to the embodiment in FIG. 4, the micromirror 103 may be held in place using a mechanical holding structure (not shown). The micromirror 103 in the embodiment of FIG. 8 may operate in the manner similar to the microprism 34 in the embodiment of FIG. 2. Thus, for example, the micromirror 103 directs the excitation photons from the laser 32 to the focusing lens 36 and, then, onto the sample 38 as illustrated in the exemplary manner in FIG. 8. The overall operation of the embodiment in FIG. 8 is substantially similar to that in FIG. 2 and, hence, additional details of various signal propagation paths, their orientations, spectral data collection, etc., are not provided herein for the sake of brevity.

It is observed here that the microprisms in the microprism-based system configurations in FIGS. 2, 4-5, and 7, or the micromirror in the micromirror-based system in FIG. 8, may act to block some of the emitted, reflected, or scattered photons received from the sample under illumination. In one embodiment, less than 2% of the photons received from the sample may be blocked by a microprism or micromirror unit. In any event, it is noted that the loss of photons received from the sample may not be significant to adversely affect the device performance. Therefore, even though the embodiment of FIG. 1 may not exhibit such a signal loss in the optical data collection path, the compactness achieved by the designs in FIGS. 2, 4-5, and 7-8 alone may be a sufficient reason to tolerate a very minimal (almost negligible) loss of signal from the sample in the designs of FIGS. 2, 4-5, and 7-8.

Figure 9:
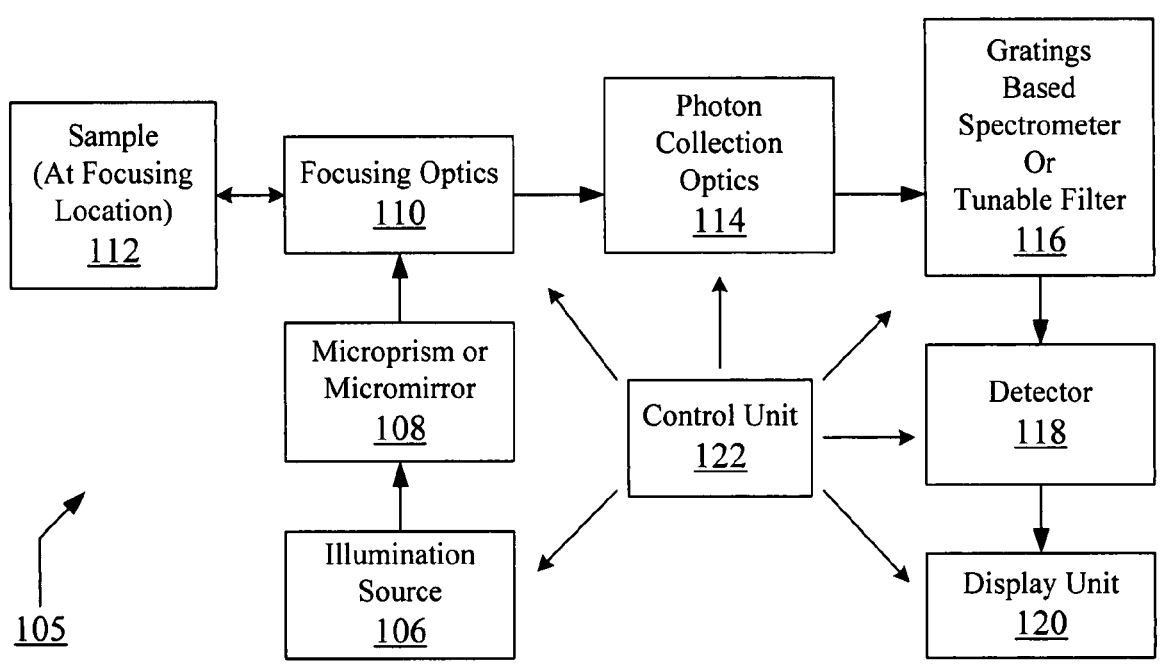
FIG. 9 illustrates an exemplary compact Raman and/or fluorescence spectroscopy system for portable or handheld spectroscopy applications according to one embodiment of the present disclosure.

FIG. 9 illustrates an exemplary compact Raman and/or fluorescence spectroscopy system 105 for portable or handheld spectroscopy applications according to one embodiment of the present disclosure. The system 105 may be a microprism or micromirror based mobile spectroscopy unit (e.g., one of the systems shown in FIGS. 2, 4-5, and 7-8) as per the teachings of the present disclosure. The system 105 may include an illumination source 106 (e.g., a laser diode, or an LED) that directly provides illuminating photons to a microprism or micromirror structure 108 that is placed in close physical proximity of a focusing optics 110. In one embodiment, the focusing optics 110 may include a single lens (e.g., in the embodiment of FIG. 2) or a combination of two or more lenses (not shown). As discussed hereinabove, a microprism may be glued to (e.g., as in the embodiment of FIG. 2) or placed in close physical proximity of the focusing optics (e.g., as in the embodiment of FIG. 4). Similarly, a micromirror may be placed in close physical proximity of the focusing optics as illustrated, for example, in FIG. 8.

When a sample 112 is placed at a focusing location of the focusing optics 110, the illuminating (or excitation) photons from the illumination source 106 are directed onto the sample 112 through the combined optical effects of the microprism/micromirror unit 108 and the focusing optics 110. The sample 112 may interact with the illuminating photons to provide reflected, scattered, or emitted photons, which photons may be initially collected by the focusing optics 110 and transferred to a photon collection optics 114. In one embodiment, the photon collection optics 114 may include another lens assembly either alone or in combination with a laser line rejection filter (e.g., as shown in the embodiment of FIG. 2). The photon collection optics 114 may direct the Raman scattered or fluorescence (emitted) photons received from the sample to a spectral selection unit 116, which may be a dispersive (e.g., gratings-based) spectrometer or an optical tunable filter (e.g., an electronically tunable liquid crystal tunable filter as shown in the exemplary embodiment of FIG. 7). An exemplary dispersive spectrometer based embodiment is illustrated in FIG. 5. The spectrometer in the spectral selection unit 116 may generate a spectrum of the sample 112 under investigation over a selected spectral range of interest. In one embodiment, the compact spectroscopy unit 105 may include a detector 118 optically coupled to the spectrometer or tunable filter 116 to generate data that can be used to display a spectral image of the sample 112. The detector 118 may receive an optical output (e.g., a wavelength-dispersed optical signal in case of a dispersive spectrometer or a wavelength-specific spectral output in case of a liquid crystal-based tunable filter) from the spectral selection unit 116 and generate signal data therefrom. The signal data may be supplied to an electronic display unit 120 to display a wavelength-specific spectral image of the sample 112 under investigation. In one embodiment, the detector 118 may a part of a spectrometer unit, in which case, the spectrometer at block 116 may include the functionality of the detector 118. In one embodiment, the detector 118 may be a charge coupled device (CCD). In another embodiment, the detector 118 may be a complementary metal oxide semiconductor (CMOS) array. In an alternative embodiment, the display unit 120 may be a computer display screen, a display monitor, or a small LCD (liquid crystal display) screen.

The compact spectroscopy system 105 may also include a programmable control unit 122, which can be suitably programmed to electronically control functionalities of one or more of the system elements including, for example, the illumination source 106, the focusing optics 110, the collection optics 114, the spectral selection unit 116, the detector 118, and the display unit 120 as shown by the exemplary illustration in FIG. 8. The control unit 122 may be a computing or data processing unit that can be suitably programmed for collecting and processing spectral information from the samples under investigation.

It is observed here that any of the exemplary spectroscopy systems of FIGS. 2, 4-5, or 7-9 may be employed as part of a handheld spectroscopy device (e.g., a handheld Raman and fluorescence detector of biothreat agents) in mobile spectroscopy applications.

The foregoing describes various embodiments of a compact Raman and fluorescence spectroscopy system that uses a microprism or micromirror based optical structure to accomplish the introduction of excitation radiation with compactness and simplified system configuration for portable or mobile spectroscopy applications. A microprism may be glued to a surface location of a focusing lens in the system to directly receive the illumination signal without intervening optical components. In one embodiment, the microprism may be simply placed in close physical proximity of the focusing lens without being glued thereto. On the other hand, a micromirror may be used instead of a microprism. The illuminating photons received by the microprism or micromirror may be directly transferred to the sample under investigation via the focusing lens. The compact system may be made portable and may further include an on-board spectrometer with or without a display unit. For chemical detecting applications, a detector (e.g., a CCD array) may also be provided along with the spectrometer.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A system comprising:
   an illumination source for providing a plurality of illuminating photons in a first direction of propagation;
   a microprism optically coupled to said illumination source to directly receive therefrom said plurality of illuminating photons in said first direction and to direct said received illuminating photons in a second direction of propagation;
   a focusing lens physically proximate to said microprism and optically coupled thereto, wherein said focusing lens is configured to directly receive said plurality of illuminating photons from said microprism in said second direction and to focus said illuminating photons onto a focusing location;
   wherein said microprism is a right angle (90°) microprism; and
   wherein said focusing lens is configured to have a lens surface that is physically closest to said right-angle microprism, and wherein said right-angle microprism is placed in close proximity of an edge of said lens surface and within a numerical aperture of said focusing lens.

2. The system of claim 1, wherein said right-angle microprism is mechanically held in a stationary position in close proximity of said edge of said lens surface.

3. The system of claim 1, wherein a right-angle forming side of said right-angle microprism is glued to a substantially flat portion of said edge of said lens surface.

4. A system comprising:
   an illumination source for providing a plurality of illuminating photons in a first direction of propagation;
   a microprism optically coupled to said illumination source to directly receive therefrom said plurality of illuminating photons in said first direction and to direct said received illuminating photons in a second direction of propagation;
   a focusing lens physically proximate to said microprism and optically coupled thereto, wherein said focusing lens is configured to directly receive said plurality of illuminating photons from said microprism in said second direction and to focus said illuminating photons onto a focusing location; and
   wherein said microprism is an equilateral microprism.

5. The system of claim 4, wherein said focusing lens is configured to have a lens surface that is physically closest to said equilateral microprism, and wherein said equilateral microprism is glued to a central location on said lens surface of said focusing lens.

6. The system of claim 5, wherein a non-triangular side of said equilateral microprism is glued to a substantially flat portion of said central location on said lens surface.

7. The system of claim 4, wherein an angle between said first direction of propagation and said second direction of propagation is other than a right angle.

8. The system of claim 4, wherein said illumination source is configured to provide said illuminating photons in said first direction of propagation that subtends an oblique angle with a lens surface of said focusing lens that is physically closest to said equilateral microprism.

9. A system comprising:
   an illumination source for providing a plurality of illuminating photons in a first direction of propagation;
   a microprism optically coupled to said illumination source to directly receive therefrom said plurality of illuminating photons in said first direction and to direct said received illuminating photons in a second direction of propagation;
   a focusing lens physically proximate to said microprism and optically coupled thereto, wherein said focusing lens is configured to directly receive said plurality of illuminating photons from said microprism in said second direction and to focus said illuminating photons onto a focusing location;
   a collection optics to collect photons scattered, reflected, or emitted from a sample when said sample is placed at said focusing location and illuminated by said plurality of illuminating photons from said focusing lens;
   a spectral analysis system coupled to said collection optics to receive a portion of said collected photons therefrom and to responsively measure a spectrum of said sample using said portion of said collected photons; and
   a detector optically coupled to said spectral analysis system to receive an output signal therefrom and to responsively provide optical data to generate a wavelength-specific spectral image of said sample.

10. The system of claim 9, wherein the detector is one of the following; a charged coupled device (CCD), and a complementary metal oxide semiconductor (CMOS) array.

11. The system of claim 10, further comprising:
    a display unit coupled to said detector to display said wavelength-specific spectral image of said sample.

12. The system of claim 11, further comprising:
    a programmable control unit, which, upon being programmed, is configured to control operations of one or more of the following:
    said illumination source; said focusing lens; said collection optics; said spectral analysis system; said detector; and said display unit.

13. A system comprising:
    an illumination source for providing a plurality of illuminating photons in a first direction of propagation;
    a microprism optically coupled to said illumination source to directly receive therefom said plurality of illuminating photons in said first direction and to direct said received illuminating photons in a second direction of propagation;

a focusing lens physically proximate to said microprism and optically coupled thereto, wherein said focusing lens is configured to directly receive said plurality of illuminating photons from said microprism in said second direction and to focus said illuminating photons onto a focusing location;

an optical filter for receiving photons emitted, scattered, or reflected from said sample and for generating a first set of filtered photons therefrom, wherein said first set of filtered photons includes those of the photons received from the sample that have wavelengths other than a wavelength of said illuminating photons;

a liquid crystal-based tunable filter to receive said first set of filtered photons from said optical filter and to generate a second set of filtered photons therefrom, wherein said second set of filtered photons include only those photons from said first set of filtered photons that have a wavelength to which said tunable filter is tuned;

a collection lens coupled to said tunable filter for sending said second set of filtered photons received from the tunable filter to a detector; and said detector coupled to said collection lens to receive said second set of filtered photons therefrom and to responsively provide optical data to generate a wavelength-specific spectral image of said sample at the wavelength to which said tunable filter is tuned.

14. A system comprising:

an excitation source for providing a plurality of excitation photons in a first direction of propagation;

a micromirror optically coupled to said excitation source to directly receive therefrom said plurality of excitation photons in said first direction and to direct said received excitation photons in a second direction of propagation;

a focusing lens physically proximate to said micromirror and optically coupled thereto, wherein said focusing lens is configured to directly receive said plurality of excitation photons from said micromirror in said second direction and to focus said excitation photons onto a focusing location;

a collection optics to collect photons reflected, scattered, or emitted from a sample when said sample is placed at said focusing location and illuminated by said plurality of excitation photons from said focusing lens;

a spectral analysis system coupled to said collection optics to receive a portion of said collected photons therefrom and to responsively measure a spectrum of said sample using said portion of said collected photons;

a detector optically coupled to said spectral analysis system to receive an output signal therefrom and to responsively provide optical data to generate a wavelength-specific spectral image of said sample; and a display unit coupled to said detector to display said wavelength-specific spectral image of said sample.

15. A method comprising:

configuring an illumination source to provide a plurality of illuminating photons in a first direction of propagation;

changing direction of propagation of said plurality of illuminating photons from said first direction to a second direction of propagation using only a microprism or a micromirror;

receiving said illuminating photons directly from said microprism or said micromirror in said second direction of propagation and focusing said illuminating photons onto a focusing location;

collecting photons reflected, scattered, or emitted from a sample when said sample is placed at said focusing location and illuminated by said plurality of illuminating photons focused onto said focusing location;

measuring a spectrum of said sample using a portion of said collected photons;

generating optical data for a wavelength-specific spectral image of said sample using said portion of said collected photons; and providing a display of said wavelength-specific spectral image of said sample.

* * * * *